United States Patent [19]
Buysch et al.

[11] Patent Number: 5,856,516
[45] Date of Patent: Jan. 5, 1999

[54] PROCESS FOR THE PREPARATION OF CARBAZOLE

[75] Inventors: Hans-Josef Buysch; Reinhard Langer, both of Krefeld; Ulrich Notheis, Dormagen; Alexander Klausener, Köln, all of Germany

[73] Assignee: Bayer Aktiengesellschaft, Leverkusen, Germany

[21] Appl. No.: 911,961

[22] Filed: Aug. 15, 1997

[30] Foreign Application Priority Data

Aug. 21, 1996 [DE] Germany ............. 196 33 609.0

[51] Int. Cl.⁶ .................................................. C07D 209/86
[52] U.S. Cl. .......................................... 548/447; 548/446
[58] Field of Search .................................. 548/447, 446

[56] References Cited

U.S. PATENT DOCUMENTS

| | | | |
|---|---|---|---|
| 2,921,942 | 1/1960 | Grotta ........................... | 548/447 |
| 3,041,349 | 6/1962 | Bearse et al. ................. | 548/447 X |
| 3,085,095 | 4/1963 | Nevitt et al. .................. | 549/447 |
| 4,628,106 | 12/1986 | Schweikert et al. ........... | 548/446 X |

*Primary Examiner*—Michael G. Ambrose
*Attorney, Agent, or Firm*—Sprung Kramer Schaefer & Briscoe

[57] ABSTRACT

Carbazole can be prepared by dehydrogenation of compounds of the formula

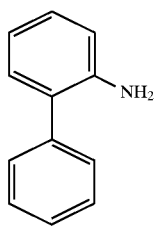
(I)

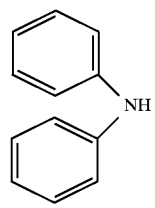

(II)

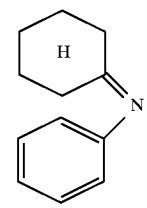

(III)

or by aminating dehydrogenation of compounds of the formula

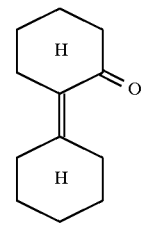
(IV)

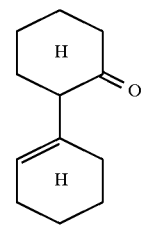

(IVa)

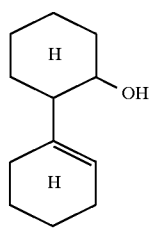

(V)

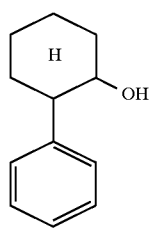

(VI)

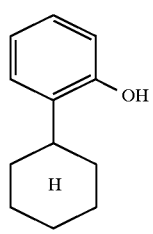

(VII)

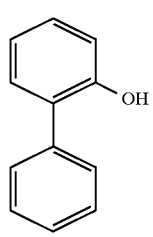

(VIII)

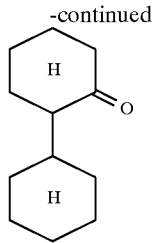 (IX)
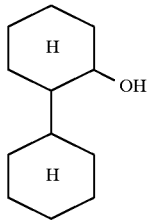 (X)
at 300° to 600° C. in the presence of hydrogen over an iridium catalyst or an iridium-containing catalyst.
20 Claims, No Drawings

PROCESS FOR THE PREPARATION OF CARBAZOLE

BACKGROUND OF THE INVENTION

1. Field of the Invention

The present invention relates to a process for the preparation of carbazole by dehydrogenation or aminating dehydrogenation of the compounds of the formulae (I) to (VIII) mentioned below in the presence of iridium catalysts or iridium-containing catalysts on supports.

Carbazole is a starting substance for the preparation of dyestuffs, polymers and insecticides (Ullmann's Encyclopedia, 5th edition, volume A5, pages 59–60).

2. Description of the Related Art

It is known that carbazole can be prepared by dehydrogenation or aminating dehydrogenation of compounds of the formulae (I) to (VIII) given below, in which parts of the carbazole skeleton are already preformed, with the aid of platinum catalysts. According to U.S. Pat. No. 2,921,942, platinum on $Al_2O_3$ or on $SiO_2$ as a support is employed in this process. Such catalysts lead to good yields of carbazole at acceptably high conversions, but after a short period of use of only a few tens of hours, even at such low loads as 0.1 g of diphenylamine per ml of catalyst and hour (g/ml.h) or even lower loads, they are already deactivated. As a result, the productivity of the catalyst, that is to say the amount of carbazole formed per hour and per ml of catalyst, even at high conversions of the diphenylamine employed, is so low that large amounts of catalyst and voluminous reactors are required for industrial purposes. Longer service lives between regenerations of the catalyst, that is to say those of several tens of hours, are obtained if magnesium oxide is chosen as the support for the platinum catalyst (U.S. Pat. No. 3,041,349). Nevertheless, the life of this catalyst is evidently only a little longer than about 150 to 200 hours in total (Table II in U.S. '349), since after a somewhat longer service life than in the above U.S. '942, that is to say a service life of about 60 or 62 hours (calculated according to the data of the diphenylamine (DPA) added in U.S. '349) between in each case two regenerations, the time before the next regeneration drops to about 17 hours, which without doubt indicates that this catalyst will soon become completely unusable. Here also, the load is only about 0.1 g/ml.h. Catalysts based on chromium oxide according to U.S. Pat. No. 3,085,095 likewise rapidly become unusable, although they tolerate somewhat higher loads.

The object of the present invention was accordingly the development of catalysts which result in good conversions and yields of carbazole under high loads and have high service lives between two regenerations, and overall a long life. It has been possible to achieve this object if iridium catalysts or iridium-containing catalysts in which other metals of the platinum metal group are employed, in addition to the iridium, are employed.

SUMMARY OF THE INVENTION

The invention accordingly relates to a process for the preparation of carbazole by dehydrogenation of compounds of the formulae

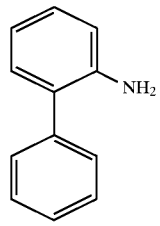

(I)

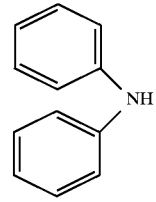

(II)

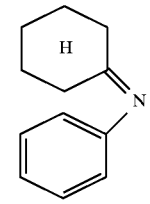

(III)

or by aminating dehydrogenation of compounds of the formulae

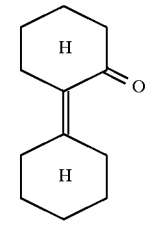

(IV)

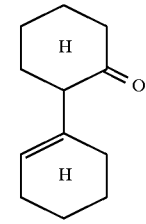

(IVa)

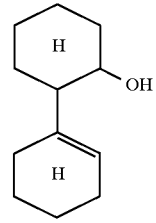

(V)

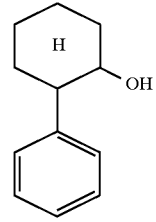

(VI)

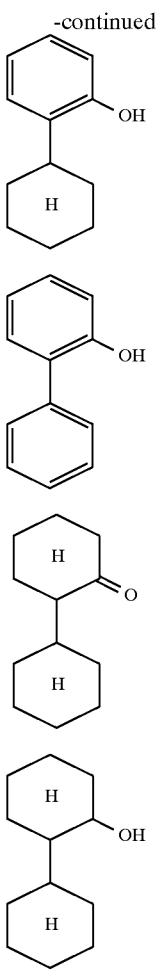

at elevated temperature over a noble metal catalyst, which comprises using an iridium catalyst or an iridium-containing catalyst at 300° to 600° C. in the presence of hydrogen.

DETAILED DESCRIPTION OF THE INVENTION

Suitable starting substances for the process according to the invention are o-phenylaniline (I), diphenylamine (II), cyclohexylideneaniline (III; the Schiff's base=anil formed from aniline and cyclohexanone), o-cyclohexylidene-cyclohexanone (IV; dianone) and its tautomer (IV), o-cyclohexyl-cyclohexanone (IX), o-cyclohexenyl-cyclohexanol (V), o-phenyl-cyclohexanol (VI), o-cyclohexylphenol (VII), o-phenyl-phenol (VIII) and o-cyclohexyl-cyclohexanol (X), preferably diphenylamine, anil, dianone, o-cyclohexylphenol and o-phenyl-phenol, particularly preferably diphenylamine.

The catalysts according to the invention comprise iridium on supports with a content of Ir of 0.01 to 10% by weight, preferably 0.1 to 6% by weight, particularly preferably 0.1 to 4% by weight, especially preferably 0.1 to 2% by weight, based on the total weight of the catalyst. Ir-containing catalysts on supports which, in addition to the content of Ir, comprise another metal from the group of platinum metals, preferably Rh, Pd or Pt, particularly preferably Pt, and in which the sum of the noble metals is 0.01 to 10% by weight, preferably 0.1 to 6% by weight, particularly preferably 0.1 to 4% by weight, especially preferably 0.1 to 2% by weight, based on the total weight of the catalyst, can furthermore be employed according to the invention; the weight ratio of Ir to the other platinum group metal is Ir: other metal=0.2 to 5:1, preferably 0.5 to 2:1.

The noble metals are applied to the support in a manner customary per se, for example by impregnation or spraying of their soluble compounds, and are fixed there by precipitation, calcining and reduction to the metals. Methods which are suitable for this are known to the expert and are described, for example, in P. N. Rylander, Catalytic Hydrogenation over Platin Metals, Academic Press 1967, pages 25 to 29 or P. N. Rylander, Hydrogenation Methods, Academic Press, 1985.

Possible soluble compounds of iridium and the other platinum group metals are simple or complex salt-like compounds, for example the halides, nitrates, acetates, acetylacetonates, carbonyl complexes and phosphine or phosphite complexes, as well as ammonia and amine complexes. Many customary organic solvents or water and mixtures thereof can be employed for application to the support; examples of organic solvents are lower alcohols, nitriles, ketones, chlorohydrocarbons, esters and amides. Of the groups of solvents mentioned, the lower members of their homologous series, for example having 1 to 4 C atoms, are chiefly employed: Water is preferable to the organic solvents because of the unproblematic processing. The supports can be treated with alkaline compounds before or after application of the noble metal solutions; treatment with alkaline compounds both before reduction of the metal salt and thereafter is likewise possible. Alkaline compounds which are suitable for this are alkaline (earth) metal hydroxides, such as NaOH, KOH, $Ca(OH)_2$ or $Ba(OH)_2$, in aqueous solution, or alkali metal carbonates, such as $Na_2CO_3$ or $K_2CO_3$, likewise in aqueous solution. During this treatment, the noble metals are precipitated as hydroxides or oxides in a known manner and fixed to the support in this way. The noble metal oxides or hydroxides which have been fixed are then reduced to the elemental metal with hydrogen. This treatment with hydrogen can in principle be carried out in the start-up phase of the process according to the invention; preferably, however, a special activation phase is provided for the catalyst, within which it is converted into the active metallic form by $H_2$ treatment.

Suitable supports for the noble metal catalysts employed according to the invention are oxides and hydroxides of elements from groups II to VIII of the periodic table of the elements (Mendeleev). Examples of elements which may be mentioned are: Mg, Ca, Ba, Zn, Al, Ga, La, Si, Sn, Ti, Zr, Nb, Ta, Cr, Fe, Co, Ni, preferably Mg, Ca, Zn, Al, Si, Sn, Ti, Zr, Nb and Cr, particularly preferably Mg, Zn, Al, Si, Ti and Zr. Other supports which can be used for catalysts which can be employed according to the invention are laminar silicates, such as bentonite and montmorillonite, and furthermore mixed oxides of the above elements, such as, for example Al/Si, Ti/Zr, Nb/Ta, Mg/Ca, Ca/Si, Mg/Si, Zn/Si, Zn/Ti and Al/Ti, which can be prepared, inter alia, by the route via mechanical mixing, joint precipitations of salts or via cogels of salts or alkoxides, such as is known to the expert (D. A. Ward et al., Ind. Eng, Chem. Res. 34 (1995), 421 to 433; W. F. Maier et al., in J. F. Harrod and R. M. Laine, Applications of Organometallic Chemistry in the Preparation and Processing of Advanced Materials, Kluwer Academic Publishers 1995, pages 27 to 46).

In the process according to the invention, at least a small amount of hydrogen is added to the starting substance of the formulae (I) to (X), although the reaction according to the invention is a dehydrogenation or an aminating dehydrogenation in which hydrogen is in principle formed. This added amount of hydrogen is 0.01 to 300 mol of $H_2$, preferably 0.1 to 200 mol of $H_2$, particularly preferably 0.2 to 150 mole of $H_2$ per mol of the compound to be dehydrogenated or subjected to aminating dehydrogenation.

While the nitrogen function is already present in the educt in the case of the compounds of the formulae (I) to (III) to be hydrogenated to form carbazole, in the educts of the formulae (IV) to (X) it must first be produced by replacing the oxygen function with the aid of ammonia. The amount of ammonia simultaneously employed which is required for this is 1 to 50 mol of $NH_3$, preferably 1.5 to 40 mol of $NH_3$, particularly preferably 2 to 30 mol of $NH_3$, per mole of the compound of the formulae (IV) to (X) to be subjected to aminating dehydrogenation.

It has furthermore been found that the presence of water is permissible in the process according to the invention, even though water is not actually necessary for carrying out the reaction according to the invention. The amount of water is therefore generally 0 to 10 mol of $H_2O$ per mole of the compound of the formulae (I) to (X) to be dehydrogenated or subjected to aminating dehydrogenation, the lower limit of zero denoting the absence of water. In the case where water is present, this can be in the range from 0.05 to 10 mol of $H_2O$, preferably 0.1 to 8 mol, particularly preferably 0.15 to 5 mol of $H_2O$ per mole of the compounds (I) to (X).

The process according to the invention is carried out in the temperature range from 300° to 600° C., preferably 350° to 580° C., particularly preferably 380° to 570° C., and in a pressure range from 0.5 to 10 bar, preferably 0.7 to 8 bar, particularly preferably 0.8 to 5 bar.

EXAMPLE 1 (preparation of the catalyst)

2 l of $\gamma$-$Al_2O_3$ (type SPH 501 from Rhone-Poulenc; beads of 3 to 4 mm $\Phi$) were impregnated with 665 ml of an aqueous solution comprising 8 g of Pt and 8 g of Ir (32 g of $H_2PtCl_6$ as a 25% strength solution and 15.4 g of $IrCl_4$) and dried in a drying cabinet at 150° C. for 24 hours. Thereafter, impregnation was carried out with 665 g of aqueous KOH solution comprising 34 g of KOH and the catalyst was dried again. The catalyst comprised 0.4% by weight of Ir and 0.4% by weight of Pt.

EXAMPLE 2 (preparation of the catalyst)

A catalyst which comprised no Pt but 1.2% of iridium was prepared analogously to Example 1.

EXAMPLE 3 (comparison)

A catalyst which comprised 1.2% of Pt was prepared analogously to Example 1.

EXAMPLE 4

A quartz tube of 1.6 mm $\Phi$ was filled with 12 ml of the catalyst according to Example 1 and the catalyst was reduced with hydrogen at 250° C. and then loaded with 0.5 g/ml.h of DPA and 100 mol of $H_2$/mol of DPA under normal pressure. A stable conversion of DPA into carbazole at 35 to 45% and a high selectivity of between 80 and 90% was obtained over a long period. After 1000 hours and continuous raising of the temperature from 350° C., the DPA conversion at 450° C., without intermediate regeneration, was still 38% at a selectivity of 87%. No signs of the onset of deactivation were to be detected.

EXAMPLE 5

The catalyst from Example 2 gave a conversion of DPA of 53% and a selectivity of 59% under the conditions of Example 4.

EXAMPLE 6 (comparison)

The catalyst from Example 3 gave a conversion of 49% and a selectivity of 38% under the conditions of Example 4.

What is claimed is:
1. A process for the preparation of carbazole by dehydrogenation of a compound of the formula

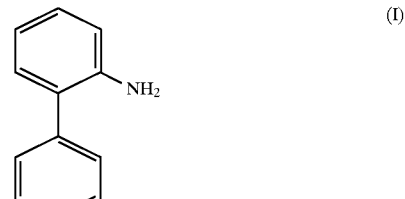

(I)

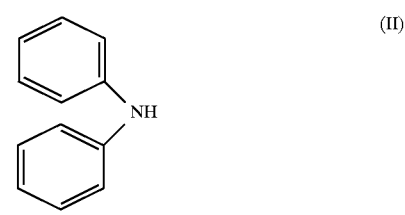

(II)

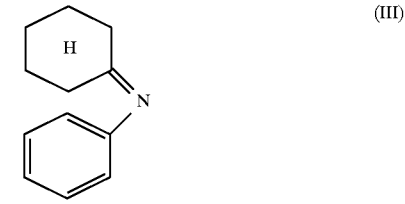

(III)

or by aminating dehydrogenation of the compound of the formula

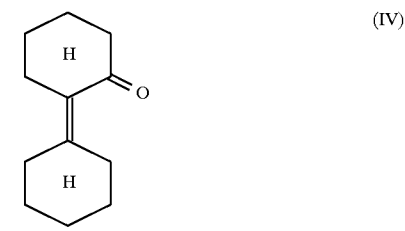

(IV)

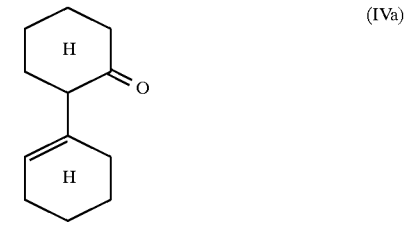

(IVa)

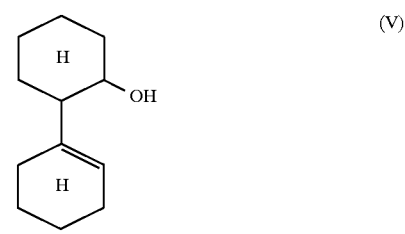

(V)

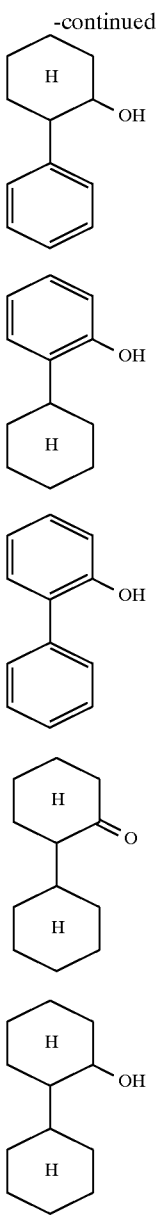

at elevated temperature over a noble metal catalyst, wherein said catalyst is an iridium catalyst or an iridium-containing catalyst having an iridium content of 0.01 to 10% by weight, based on the total weight of the catalyst, at a temperature of 300° to 600° C. in the presence of hydrogen.

2. The process of claim 1, wherein the content of iridium in the iridium-containing catalyst is 0.1 to 6% by weight.

3. The process of claim 2, wherein the content of iridium in the iridium-containing catalyst is 0.1 to 4% by weight.

4. The process of claim 3, wherein the content of iridium in the iridium-containing catalyst is 0.1 to 2% by weight.

5. The process of claim 1, wherein the catalyst is an iridium-containing catalyst in which, in addition to the iridium, another platinum-group metal is present, the sum of said iridium and said other platinum group metal being 0.01 to 10% by weight, based on the total weight of the catalyst, and the weight ratio of iridium to the other platinum group metal=0.2 to 5:1.

6. The process of claim 5, wherein the other platinum-group metal is rhodium, palladium or platinum.

7. The process of claim 6, wherein the other metal is platinum.

8. The process of claim 5, wherein the sum of said iridium and said other platinum group metals is 0.1 to 6% by weight, based on the total weight of the catalyst.

9. The process of claim 5, wherein the weight ratio of iridium to the other platinum group metal is 0.5 to 2:1.

10. The process of claim 1, wherein a compound of the formula (II), (III), (IV), (VII) or (VIII) is employed as the compound to be dehydrogenated or subjected to aminating dehydrogenation.

11. The process of claim 1, wherein 0.01 to 300 mol of $H_2$ is present per mole of the compound to dehydrogenated or subjected to aminating dehydrogenation.

12. The process of claim 11, wherein 0.1 to 200 mol of $H_2$ per mole of said compound is present.

13. The process of claim 1, wherein, in said aminating dehydrogenation, 1 to 40 mol of $NH_3$ per mole of the compound to be subjected to aminating dehydrogenation is present.

14. The process of claim 13, wherein 1.5 to 40 of $NH_3$ is present.

15. The process of claim 14, wherein 2 to 30 mol of $NH_3$ is present.

16. The process of claim 1, wherein the reaction is carried out at a temperature of 350° to 580° C.

17. The process of claim 16, wherein the reaction is carried out at a temperature of 380° to 570° C.

18. The process of claim 1, wherein the reaction is carried out at a pressure of 0.5 to 10 bar.

19. The process of claim 18, wherein the reaction is carried out at a pressure of 0.7 to 8 bar.

20. The process of claim 19, wherein the reaction is carried out at a pressure of 0.8 to 5 bar.

* * * * *

UNITED STATES PATENT AND TRADEMARK OFFICE
CERTIFICATE OF CORRECTION

PATENT NO. : 5,856,516
DATED : January 5, 1999
INVENTOR(S) : Buysch, et al.

It is certified that error appears in the above-identified patent and that said Letters Patent is hereby corrected as shown below:

Title page, item [57] ABSTRACT: Line 2 and line 7 delete " formula " and substitute -- formulae --

Col. 8, line 29   After " to " insert -- be --

Col. 8, line 36   After " 40 " insert -- mol --

Signed and Sealed this

Nineteenth Day of October, 1999

Attest:

Attesting Officer

Q. TODD DICKINSON

Acting Commissioner of Patents and Trademarks